US009058733B2

(12) United States Patent
Brinkley et al.

(10) Patent No.: US 9,058,733 B2
(45) Date of Patent: Jun. 16, 2015

(54) SECURITY FILM

(71) Applicants: Kenneth Brinkley, Owenton, KY (US); Robert Ufer, Punta Gorda, FL (US)

(72) Inventors: Kenneth Brinkley, Owenton, KY (US); Robert Ufer, Punta Gorda, FL (US)

(73) Assignee: Select Engineering Services LLC, Punta Gorda, FL (US)

( * ) Notice: Subject to any disclaimer, the term of this patent is extended or adjusted under 35 U.S.C. 154(b) by 0 days.

(21) Appl. No.: 13/815,703

(22) Filed: Mar. 14, 2013

(65) Prior Publication Data

US 2013/0265156 A1 Oct. 10, 2013

Related U.S. Application Data

(63) Continuation-in-part of application No. 12/321,941, filed on Jan. 27, 2009, now abandoned.

(60) Provisional application No. 61/062,628, filed on Jan. 28, 2008.

(51) Int. Cl.

| | |
|---|---|
| ***G08B 1/08*** | (2006.01) |
| ***B32B 3/00*** | (2006.01) |
| ***G08B 25/01*** | (2006.01) |
| ***G08B 13/12*** | (2006.01) |
| *G08B 1/00* | (2006.01) |
| *G08B 13/14* | (2006.01) |
| *A61B 5/04* | (2006.01) |
| *F41H 1/02* | (2006.01) |
| *A41D 13/015* | (2006.01) |
| *G08B 7/06* | (2006.01) |
| *G08B 25/00* | (2006.01) |

(52) U.S. Cl.
CPC ............ *G08B 25/016* (2013.01); *G08B 13/126* (2013.01); *F41H 1/02* (2013.01); *G08B 7/066* (2013.01); *G08B 25/009* (2013.01)

(58) Field of Classification Search
USPC .............................................. 340/539.13, 541
See application file for complete search history.

(56) References Cited

U.S. PATENT DOCUMENTS

| | | | | |
|---|---|---|---|---|
| 5,636,378 | A * | 6/1997 | Griffith | 2/455 |
| 2005/0148320 | A1* | 7/2005 | Tanabe | 455/411 |
| 2008/0075934 | A1* | 3/2008 | Barlow et al. | 428/199 |
| 2010/0083733 | A1* | 4/2010 | Russell et al. | 73/12.01 |
| 2014/0130225 | A1* | 5/2014 | Balzano | 2/2.5 |

FOREIGN PATENT DOCUMENTS

| | | | |
|---|---|---|---|
| WO | WO 2008069682 A1 * | 6/2008 | G01L 5/00 |

* cited by examiner

*Primary Examiner* — Jack K Wang

(74) *Attorney, Agent, or Firm* — Richard B Klar; Law Office Richard B Klar

(57) ABSTRACT

A tamper indication device has a film attached and connected within the circuit that generates a signal in response to a tamper event. The tamper indication device can be incorporated into a bullet proof vest. The sensor circuit in the bullet proof vest does not only detect a bullet strike but also determines the location of the strike base in the sensor zone where the sensor zone has been struck. This circuitry includes a cell phone module with a built in GPS sensor for supplying GPS coordinates and communicating by dispatcher with the vest wearer's name and other identifying information.

12 Claims, 14 Drawing Sheets

Current Prototype System Architecture

Direct Descendant Second Generation Prototype

SECURITY FILM

RELATED APPLICATIONS

The present application is a continuation in part of Ser. No. 12/321,941 filed Jan. 27, 2009 and claims priority thereunder 35 USC 120 which in turn claims priority of provisional patent application 61/062,628 filed on Jan. 28, 2008.

BACKGROUND

The present disclosure relates generally to a flexible security film and monitoring device that can detect and provide a real time alert, signaling the film has been tampered with or penetrated.

It is highly desirable to have an accurate method of determining and signaling exactly when tampering or penetration occurs. It is often difficult to accomplish this without triggering false alarms; items protected using current technology only tell you they were tampered with after they have been received and the tamper indicator has been inspected. They do not signal that they have been tampered with at the time of occurrence.

Security concerns exist for all types of packaging that contains high value items/goods; envelopes, crates, containers, or pallets that are shipped by carriers, air ship etc. All goods are susceptible to pilfering or tampering during transport or storage in unsecured areas.

To date there have been various attempts to provide monitoring and security. The use of dye when exposed to air changes color to let one know if someone has compromised the envelope or package. This provides a tamper indicator that has a small deterrent factor for honest employees.

However, these approaches do nothing for the user but to let the user know someone has tampered with the user's goods, which would be discovered upon opening the goods anyway.

Some of these approaches can result in a false trigger leaving the user with doubt in the carrier's ability to properly handle the package.

SUMMARY

The present disclosure seeks to overcome the aforementioned drawbacks of the prior art proposal by utilizing a low cost RFID unit in concert with the film to send an instantaneous alert the moment tampering occurs. This greatly increases the chance of recovery and identifying the weak links in the system that plague the company with unnecessary loss at the high cost of loss of revenue and reputation. Additionally, the films unique properties are used with a communication link that can utilize a variety of RF technologies such as but not limited to passive and active RFID Tags and also use hard wired communications to name a few.

The present disclosure provides for a tamper indication film that is responsive to a variety of tampering methods. A tamper indicative film can provide an output as a visually or audibly perceptible display or as a feed to a data collection system such as a computer. It can provide a tamper indication that can be used on different sized envelopes and containers.

It can provide a tamper indication in remote areas using cellular or other communication links to provide remote security utilizing the security film which can be formed by way of illustrative but non-limiting example by a wall paper, into a sensor that can be used to provide a 3 dimensional model/rendering of the building or multiple buildings completely scalable from top view of a city both internally and externally, covering the walls, ceiling and floor. Utilized in this manner one can automate or eliminate the "human factor" and provide life saving critical information to one master computer or network the pertinent data information to all users. This unique method/capability when applied to current building using cameras, smoke/gas/chemical detectors/sniffers of allows the user to build an unmanned automatic response system providing "situational awareness" where the smoke/fire/structure is intact or destroyed in near real time greatly increasing the chance of survival over the current static emergency exit map that just tell one the closest way out of the building but does not take in account that the danger can be in route of the closest way out and could be the map that can kill someone. It is a well known fact most people die of smoke inhalation. This data can be sent to a smart phone and display this critical information turning the smart phone into a "Fire/danger compass" guiding one to the safest way out. Essentially providing the would be victims with the tools to save themselves. Basically, this frees up first responders to save the people who are non ambulatory personal or personal who cannot not save themselves. With the film substrate, material or tape, a user has the ability to provide low power to the tamper indicative device of the present disclosure, for example with an AA size lithium battery that could provide 24 hour security to the item it is attached to for ten years. Alternatively, a printable battery can be used. If the RFI tags are passive the charge for the RFID tag can be induced.

Additional benefits are the system can take into account not only the structural integrity of the building but provide automated responses, networking current sensors/detectors/sniffers i.e., smoke, heat, chemical, nuclear, biological and pressure water, gas, fuel, electrical. By plugging this into a 3-d model not only does one have a top view as described above but also enables complete control over natural and manmade disasters, to minimize damage and loss of vital assets. Example: Upon the detection of the event FIRE—The system could close off vents, shut off fuel, unlock/lock security doors direct the security cameras where to look automatically. This is preferable compared with the current method of a human having to call a 911 operator and the secondary call from the 911 operator to a command center, that then has to search by camera to verify the information, then the commander makes decisions based on the intel at that time. Much like a fluid battlefield the situation can change in minutes and could make the last decisions invalid causing a delay in the appropriate response further endangering property and personnel.

The tamper security device of the present disclosure that can be used for small packages is independent of other security systems such as those utilized for an office building or a house where the packaged item in question—the item for which the tamper security device is to be attached to—is located. Thus an authorized user may disable the home or office security to permit someone else to have access within the location where the item to be protected by the tamper security device is located but still have security control via the tamper security device over that particular item. This eliminates pilfering by limiting access to the personal item. Studies have shown that 90% of most thefts are opportunistic.

Additional objects, advantages and other novel features will be set forth in part of the description that follows and in part will become apparent to those skilled in the art upon examination of the following or maybe learned with practice of the present disclosure.

As described herein, there is a tamper indication device having a film attached and connected within the circuit that generates a signal in response to a tamper event. The signal is received by a micro-controller which generates an output signal to a display or data collection device and transceiver. The output signal can take information from a variety of different sensor types, i.e. shock; vibration, temperature, sniffers (Nuclear/Biological/Chemical), smoke, pressure (Water/Fuel/Gas) and security breach information and display it in a data collection device.

In another embodiment of the present disclosure a tamper indication device can be incorporated into a bullet proof vest. The sensor circuit 6 in the bullet proof vest cannot only detect a bullet strike or sharp object, knife, blade, ice pick but also determines the location of the strike based on the where in the sensor zone it has been struck. This circuitry includes a cell phone module with a built in GPS sensor for supplying GPS coordinates (text messages) and communicating by dialing the 911 dispatcher with the vest wearer's name and other identifying vital information. A microphone can be added to provide the 911 dispatcher with audio monitoring of the scene.

Still other objects of the present disclosure will become apparent to those skilled in this and from the following description wherein there is shown and described in the preferred embodiment of this invention, simply by the way of illustration of one of the best modes contemplated for carrying out the present disclosure. As will be realized, the present disclosure is capable of different embodiments, and its several details are capable of modification in various, obvious aspects all without departing from the invention. Accordingly, the drawings and descriptions will be regarded as illustrative in nature and not as restrictive.

Reference will be made in detail to the present preferred embodiment(s) of the invention, an example of which is illustrated in the accompanying drawings

DETAILED DESCRIPTION OF THE PREFERRED EMBODIMENTS

Figure 1:
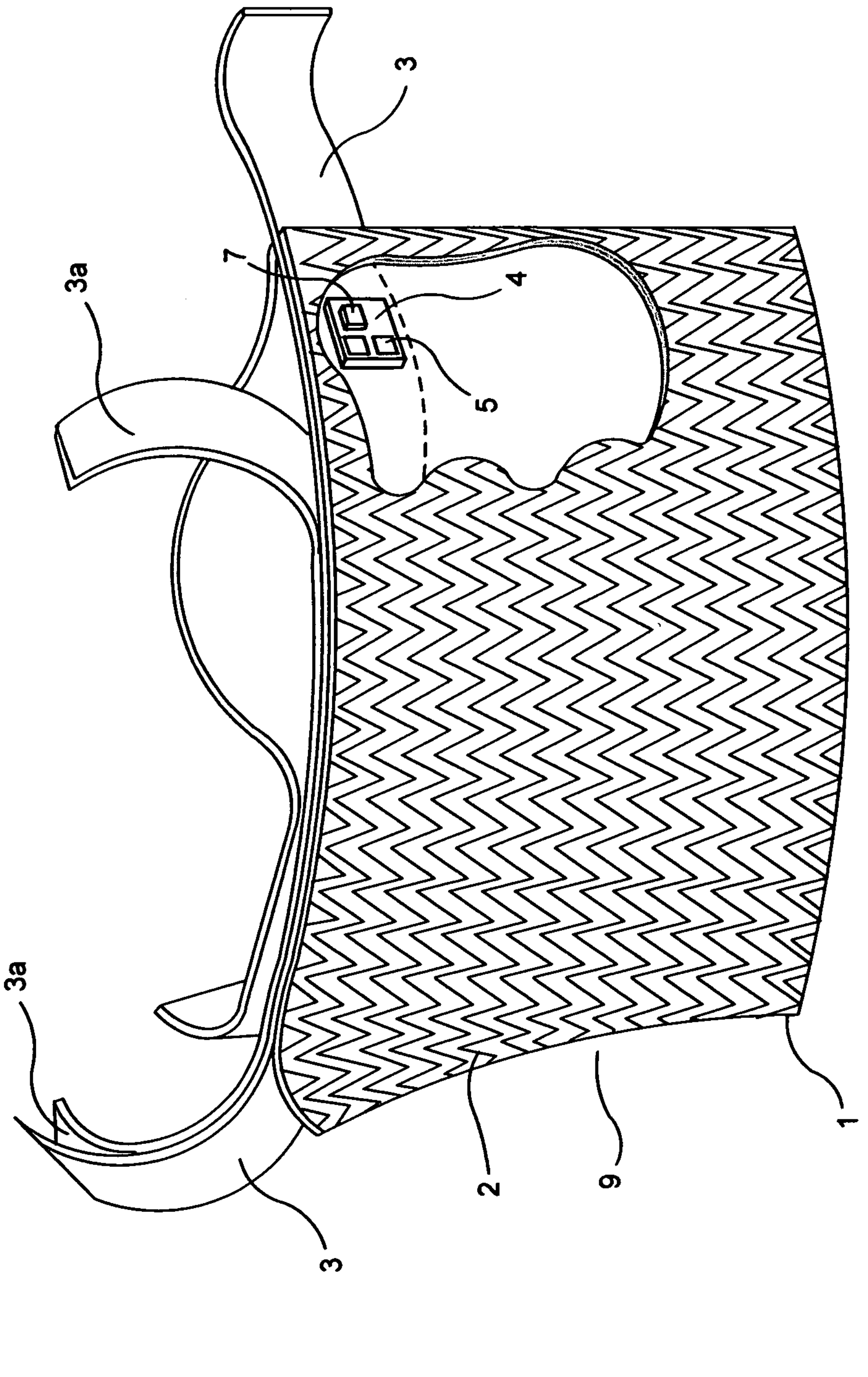
FIG. 1 is a perspective view of a tamper indication device incorporated into an enclosure such as bag or a pouch according to the present disclosure.

Referring now to the drawings in detail, wherein like numerals indicate the same elements throughout the views, FIG. 1 shows a diagrammatic representation of the various components of a tamper indication device constructed in accordance with the present invention. The tamper indication device 1, includes a sensing element formed as a conductive patterned printed layer of film laminate 2 (shown by way of non-limiting illustrative example in a zig zag pattern in FIG. 1), a two-sided conductive tape 3, a RFID passive or active tag 7, a peel off adhesive strip (3*a*) to close the circuit, component pad 5 on the RFID Housing 4, a battery 6 (shown in FIG. 2 and not shown in FIG. 1). Peeling off the adhesive conductive strip 3*a* serves two purposes; first it seals an enclosure such as the security pouch or bag 9 shown in FIG. 1 and secondly it completes the circuit between the tamper indication device 1 and the RFID Tag. 7. It is understood that the present disclosure is not limited to any particular enclosure and the embodiment shown in FIG. 1 is a non-limiting illustrative example of the type of enclosure for which the invention can be utilized. When a Passive RFID tag 7 is used an authorized user can detect a circuit break by passing the tamper indication device 1 (Security Film) through a data collection device, such as an RFID Reader, from point to point. When the RFID tag 7 is an active tag the sealing of the security film using the conductive strip completes the circuit and starts a clock in the active tag 7, it can also activate other sensors in conjunction with it such as one or more GPS units. When the circuit or security envelope or other barrier is broken the system provides an instantaneous alert via the Active RFID Tag 7. The RFID tag 7 is connected to the film laminate 2. The conductive adhesive tape 3 seals the pouch when the peel off strip 3*a* is removed. The film laminate surrounds the pouch on the front and rear surfaces so that tampering such as a tear or rip will be detected as well as an opening of the pouch where sealed by the adhesive from the peel off strip. When such tampering occurs, the active RFID tag 7 will send a signal to a data collection device informing a person at the data collection site of the tampering of the pouch. The conductive pads 5 preferably are adhesively coated to provide an adhesive for where the pads 5 connect with the bag or pouch 9. The side of the housing 4 where the RFID tag 7 or the transponder 7 is located can also be adhesively coated for an adhesive contact with the back side of the two sided tape 3 or alternatively, if preferred with the bag or pouch 9. It is possible to use more than one RFID tag 7 or transponder 7 if desired.

Figure 2:
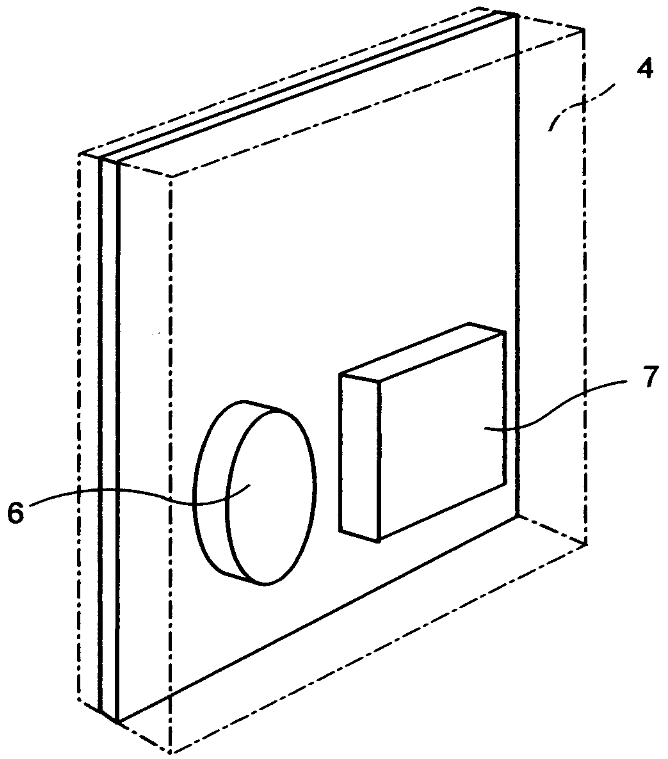
FIG. 2 is a perspective view of a transponder or RFID tag device 7 of FIG. 1.

FIG. 2 illustrates the housing for the RFID Tag of the embodiment in FIG. 1. The housing 4 includes on its faces a battery 6 and an RFID tag 7.

The tamper indication device 1 in FIG. 1 generates an electrical signal, such as the breaking of an electrical circuit, in response to each time the film is penetrated, which occurs when the object enclosed, is tampered with. The film laminate 2 is electrically connected to the RFID tag 7 via pads 5 connected to housing 4, adapted to detect a break in the circuit causing the RFID tag 7 to generate an output signal either by, to a data collection device in response to receipt of this signal. Battery 6 provides power to the tamper indication device 2. This RFID tag 7 as noted herein can alternatively be a micro-controller or any other transponder where the transmission of the signal can be sent by RF, IR or inductively transmitted.

Referring to FIG. 2, the tamper indication sensing assembly 1, shown in section view, that can be inserted into a housing such as an envelope or alternatively as shown in the tamper sensing assembly 2 can be formed integrally with the housing 1 (as shown in FIG. 1) or can be employed separately by using the tape 3 with the transponder 7 or RFID Tag 7 for a door that is opened or tampered with, etc. A sensor element is electronically connected to the micro-controller or RFID tag 7. The tamper indication device 1 detects unauthorized users, but preferably not in response to authorized users. Preferably, this electrical circuit is closed only once when the items are placed internally within the protective security film. An AA lithium battery 6, by way of non-limiting illustrative example, can be attached and could provide power to the device and security for 10 years. Alternatively, a printable battery can be used. If the RFID tags 7 are passive the charge for the RFID tag can be induced. A printable battery or for a passive RFID tag 7 inductive charge can be used for the embodiment of FIG. 1 as well.

Figure 3A:
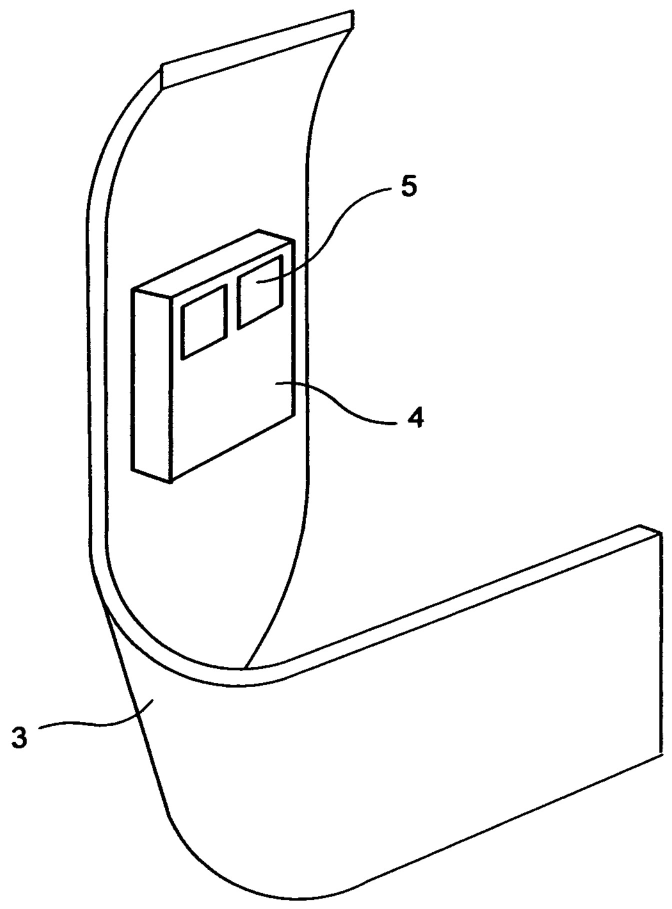
FIG. 3 A is a portion of the two sided tape 3 showing one side of the housing 4 for the transponder 7 or RFID tag 7 mounted thereon where the contact pads 5 are shown.
FIG. 3B is a portion of the two sided tape 3 showing another side of the housing 4 for the transponder or RFID tag 7 mounted behind the two side tape 3 with battery 6 and RFID Tag 7 showing in visible lines behind the tape 3 thereon where the contact pads 5 are shown.
Figure 3B:
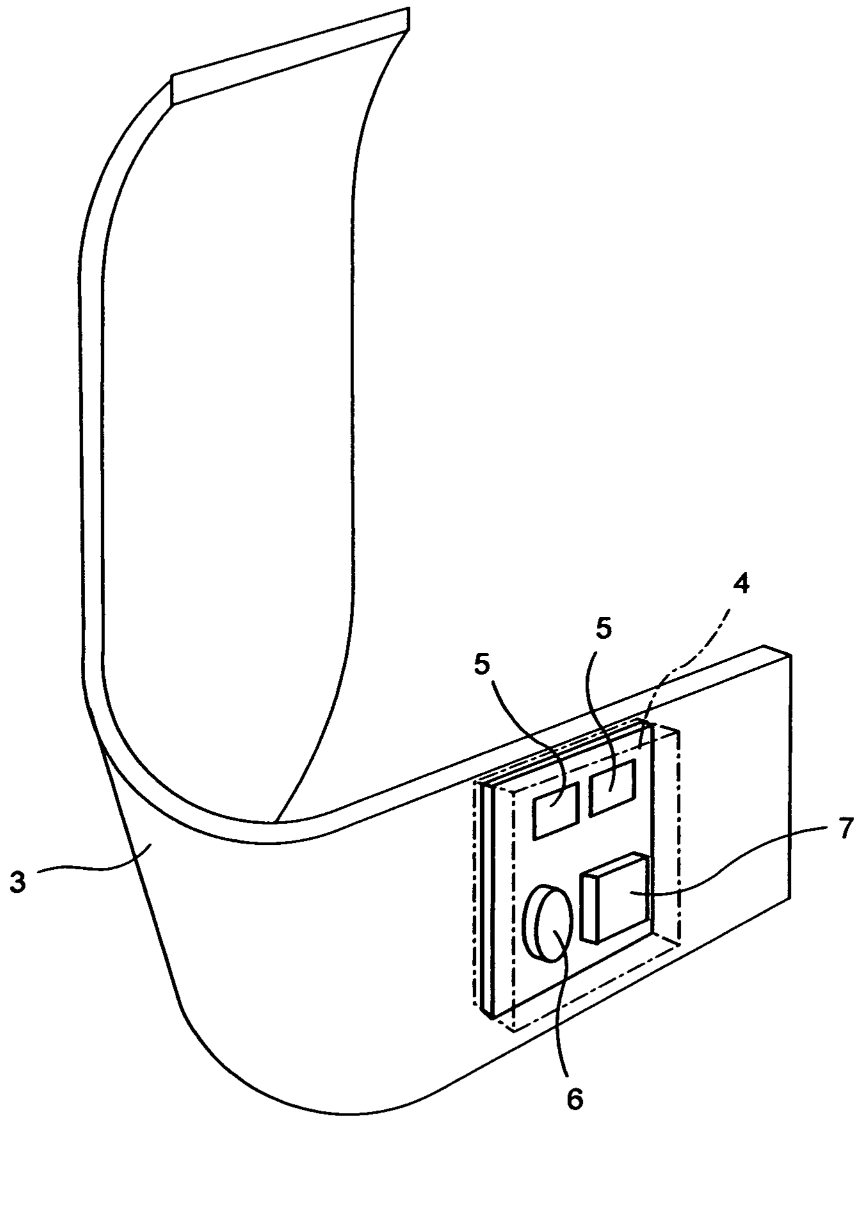

FIGS. 3A and 3B show the two sides of the housing 4 for the transponder 7 that is mounted on the two sided tape 3. In FIG. 3A the housing 4 is shown in which the contact pads 5 are located on the transponder or RFID tag 7. The side of the pads 5 makes electrical contact with and are preferably adhesively applied to the bag or pouch 1 to make and close the circuit with the film laminate 2.

It is understood that the present disclosure is not limited to enclosures protected by the tamper indication device 1 of the present disclosure but can include any other item that one wishes to protect by providing the mechanism of the present disclosure for alerting someone when that item is being tampered with and also storing the tampering information within the transponder.

The film laminate 2 can be formed by printable conductive ink that can be printed on any surface including but not limited to Mylar film, plastic, flexible material, cloth etc. The ink is preferably a silver filled polymer ink such as 112-15 by Creative Material Inc. or any other suitable commercially available ink. The ink would preferably have the following characteristics or attributes a viscosity 12,000 CPS @ 30 C; a total solids content 61%; a density 17 lbs/gal; a flash point 212 F; VOC 794 Grams of solvent/liter; an electrical resistance <0.015 ohms/square @ 1.0 Mil; and an electrical resistance <0.015 ohms/square @ 25.4 microns. The ink would be durable and thus unlikely to break unless the film laminate 2 is tampered thus avoiding a false triggered alarm.

Figure 4C:
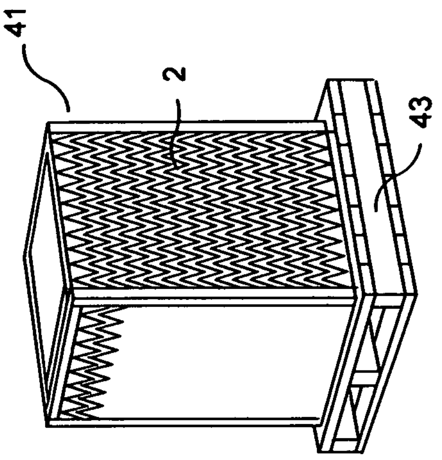
FIGS. 4A, B and C show an embodiment of the present invention in which the tamper indication device is placed in goods on a pallet.
Figure 4B:
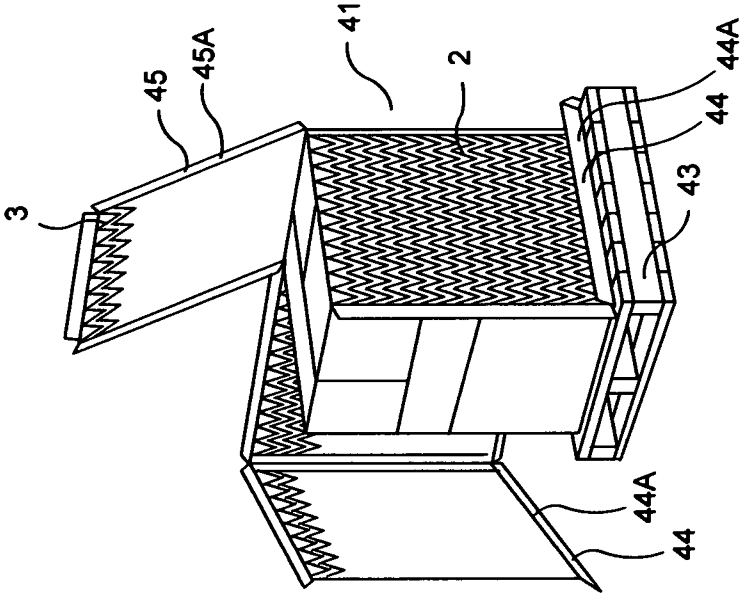
Figure 4A:
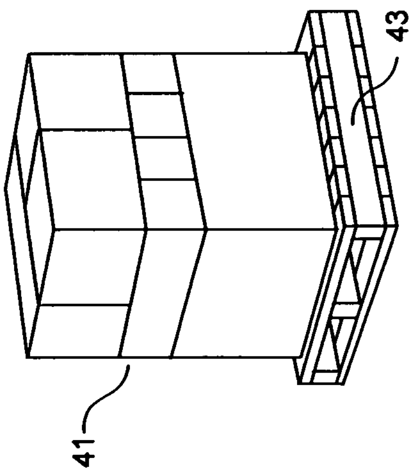

An embodiment of the present disclosure would be for palletized goods as shown in FIGS. 4A, 4B and 4C where a flexible fabric type material or film laminate 2 with the conductive ink printed thereon and connected to the transponder (not shown) as described for FIGS. 1 and 2 would be placed over a container or box 41 for goods on a pallet 43 and the less than one percent stretchable flexible fabric type material 2 could be covered by stretch wrap, shrink wrap, banded or covered by a box or container 41 to keep the goods in place. The box 41 would have flaps such as flaps 44 and 45 as shown in FIG. 4B in which electrically conductive double sided tape 3 would be placed on a face 44*a* (for flaps 44 and 45*a* for flap 45 and peeled off and then flap 44 would be paced against the side of the pallet 43 to and flap 45 against the top surface of 46 of box 41 to seal the circuit in place so that a breach can be detected. It is noted that allowance is made for holes on the side of 43*a* where flaps 44 are placed for fork lifting the pallet 43 without breaching the tamper indication device 1 by allowing holes in the flap 44 that do not trigger the system. If the fabric or film laminate 2 is penetrated or opened to gain access to the goods this intrusion would be detected and a signal sent out. The film laminate 2 is preferably made of a flexible film that does not stretch by human hand and has a film stretch of far less than 1 percent if a human hand tried to stretch the film by pulling it. The film can be 0.010" thick polyester film provided by Creative Materials Inc. or a DuPont Teijin film grade Melinex 618, thickness 100 film or a DuPont Kapton polymide film minimum of 2 mills thick or any other suitable commercially available film. The virtually unstretchable film prevents a thief from gaining access to the pallet or goods by stretching the film and reaching underneath it. This is a very desirable feature that is not available using stretchable laminates offered by others.

There are numerous types of outputs possible with the open architecture designed into the system. It can easily be configured to provide audible alerts as well as silent alerts within microseconds of the unauthorized event/entry into FIG. 1. Inside the tamper indication device housing contains all the necessary hardware and communication capability that interfaces with the film through a flex connector.

Figure 5A:
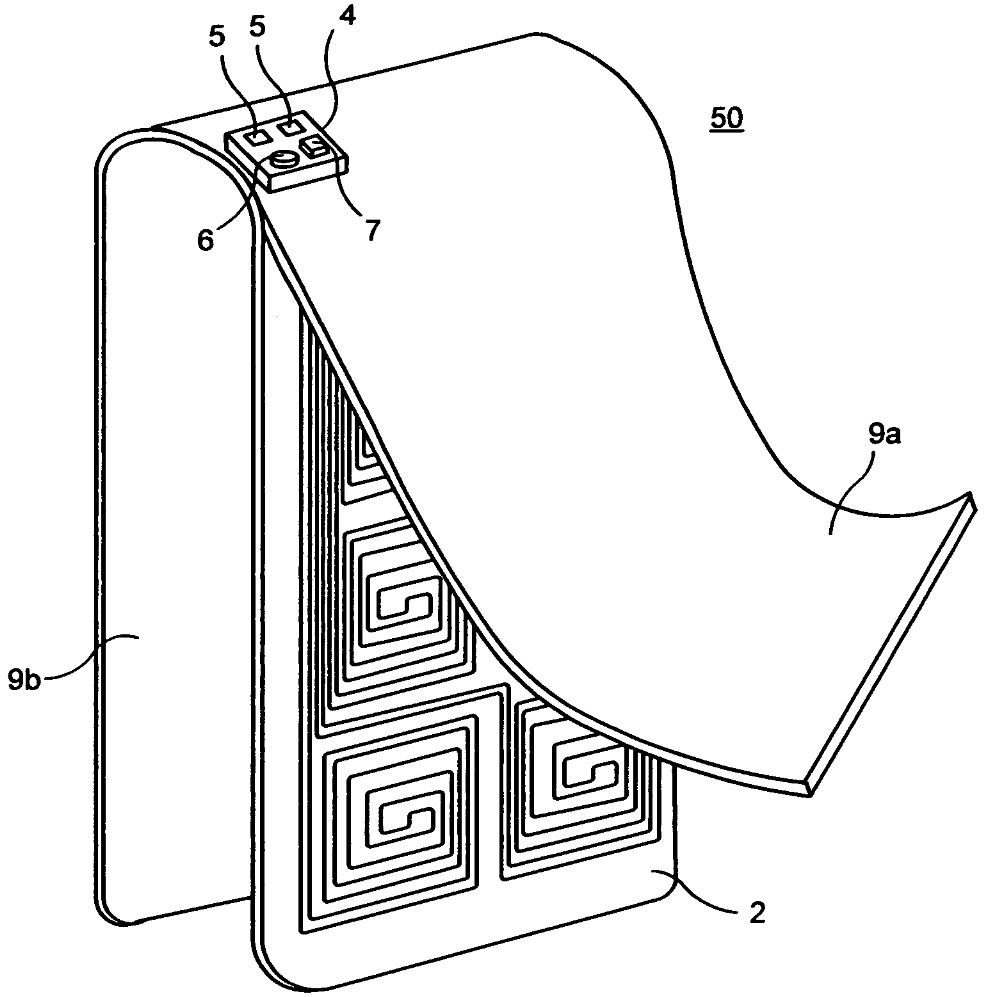
FIG. 5A shows another embodiment of the present disclosure in which the tamper indication device 1 can be incorporated into a bullet proof vest.

FIG. 5A. is a perspective view of a first embodiment of a bullet proof vest 50 for the present disclosure. The bullet proof vest 50 has a front panel 9*a* and a rear panel 9*b*. The vest 50 includes a sensing element formed as a conductive patterned printed ink layer of film laminate 2. An RFID passive or active tag 7, a component pad 5 on top of the RFID Housing 9 and a battery 6 serve to complete the circuit between the vest 50 and the RFID tag 7. When there is a breach, break or tampering of the film laminate such as due to a bullet strike, the RFID Tag 7 will send a signal to a data collection device informing a person at the data collection device of the breach, break tampering or bullet strike with the film laminate 2. The materials and structure is the same or similar to that described in FIGS. 1-4 of the present disclosure.

Figure 5B:
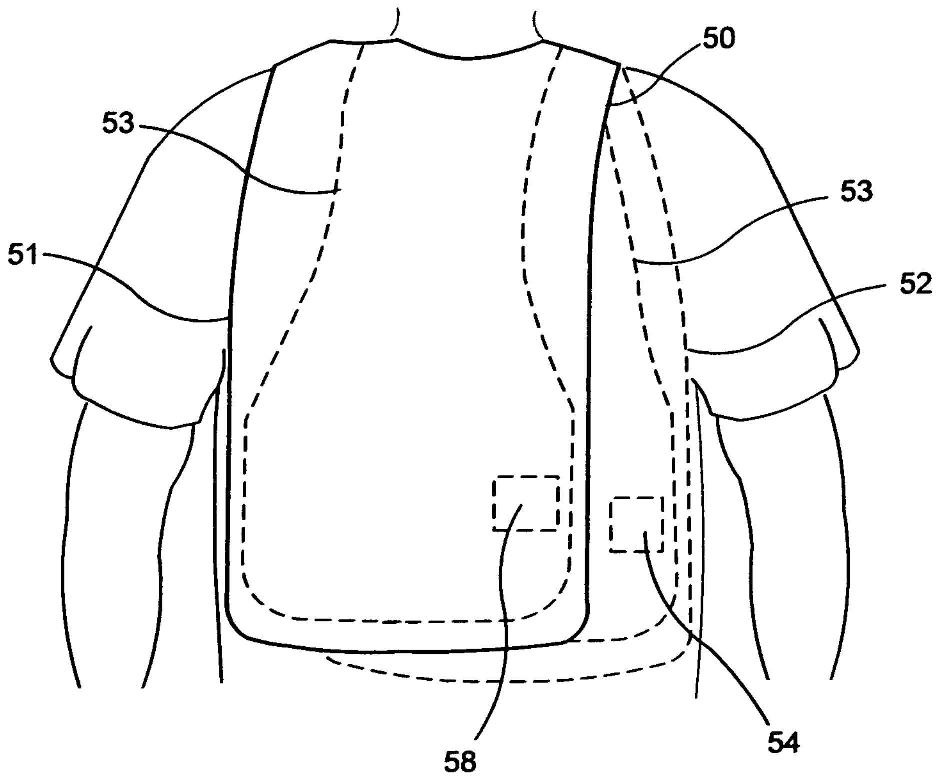
FIG. 5B shows another embodiment of a bullet proof vest for the present disclosure in which a cellular module is incorporated into the front panel and a blue tooth device is incorporated into the back panel of the bullet proof vest.

Additional embodiments of the present disclosure are shown in FIGS. 5*b*-9*b*. As shown in FIG. 5*b* the tamper indication device 1 can be incorporated into a bullet proof vest 50 acting as a sensor (not shown) for when a bullet penetrates the vest 50 and sets off the security film by breaching it with the bullet's penetration therein. A police officer wearing a bullet proof vest 50 may be able to have the vest 50 stop the bullet from completely penetrating through his body; however the officer still may suffer from trauma due to the impact from the bullet hitting the bullet proof vest and even knocking the officer over causing incapacitating injuries. If the police officer is working on a lone patrol, he may be hurt and unable to call for help due to the trauma suffered from bullet. Under these circumstances the tamper indication device 1 of the present application works like a sensor not only detecting the bullet strike but also making it possible to determine the location of the bullet. This application of the tamper indication device 1 of the present application works in the military as well as for providing a low cost bullet detection sensor. As shown in FIG. 5B the Bullet Proof vest application preferably includes two separate panels 51, 52 per vest 50. One or more electrically conductive sensor circuits are printed on each panel 51, 52. The sensor circuit not only detects the bullet strike but also determines the location of the strike based on which sensor zone has been struck. The use of two separate panels 51, 52, such as a front panel 51 and a back panel 52, not only allows the vest 50 to be incorporated into new bullet proof vests 50 but also allows the two panels 51, 52 to be retrofitted into existing ones. Current bullet proof vests 50 consist of a carrier 53, which is the outer layer of fabric that contains a pocket into which the bullet proof material is inserted, and the ballistic inserts. The sensor circuit is inserted into the carrier in the same manner as the ballistic inserts. The back panel 52 as shown in FIG. 5 B houses only a Bluetooth Low Energy (BLE) radio 54 or any other RF communications device such as Zigbee or RFID which senses trace integrity and communicates with the other panel's BLE radio. The front panel 51 (see FIG. 5*b*) additionally incorporates a cell phone module 55 with a built in GPS sensor, which when activated by the BLE radio 54, supplies the GPS coordinates and either calls 911, or sends a text message to 911 or a dispatcher with the wearer's name and other identifying information. For law enforcement an optional version would then open a microphone (not shown) and continuously transmit audio information once the system is activated until the battery dies.

Figure 6:
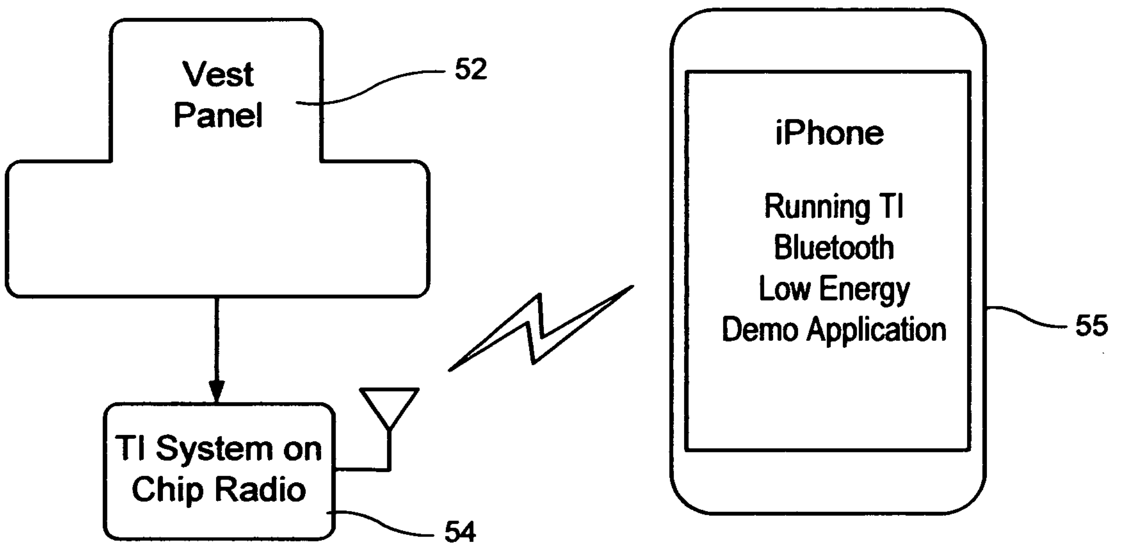
FIG. 6 shows the embodiment of the bullet proof vest of FIG. 5 of the present disclosure utilizing Bluetooth technology such as but not limited to a TI Bluetooth Low Energy (BLE) system on a chip (single chip with processor, radio, and supporting peripherals); sensors for sound, video and defibulators, etc.

As shown in FIG. 6 the bullet proof vest panel 52 of the present disclosure can utilize Bluetooth technology such as but not limited to a first generation TI Bluetooth Low Energy (BLE) system on chip 54 (single chip with processor, radio, and supporting peripherals). It is understood that other technology including other generations of Blue tooth technology may be employed as is known in the art.

Vest electronics may be modified as is known in the art to be compatible with existing firmware, thus no changes required to existing source or compiled code Demonstration, iPhone application with slightly modified source code. The bullet proof embodiment of the present disclosure is useful for determining technology and fabrication techniques required to pass NIJ test protocol.

Figure 7:
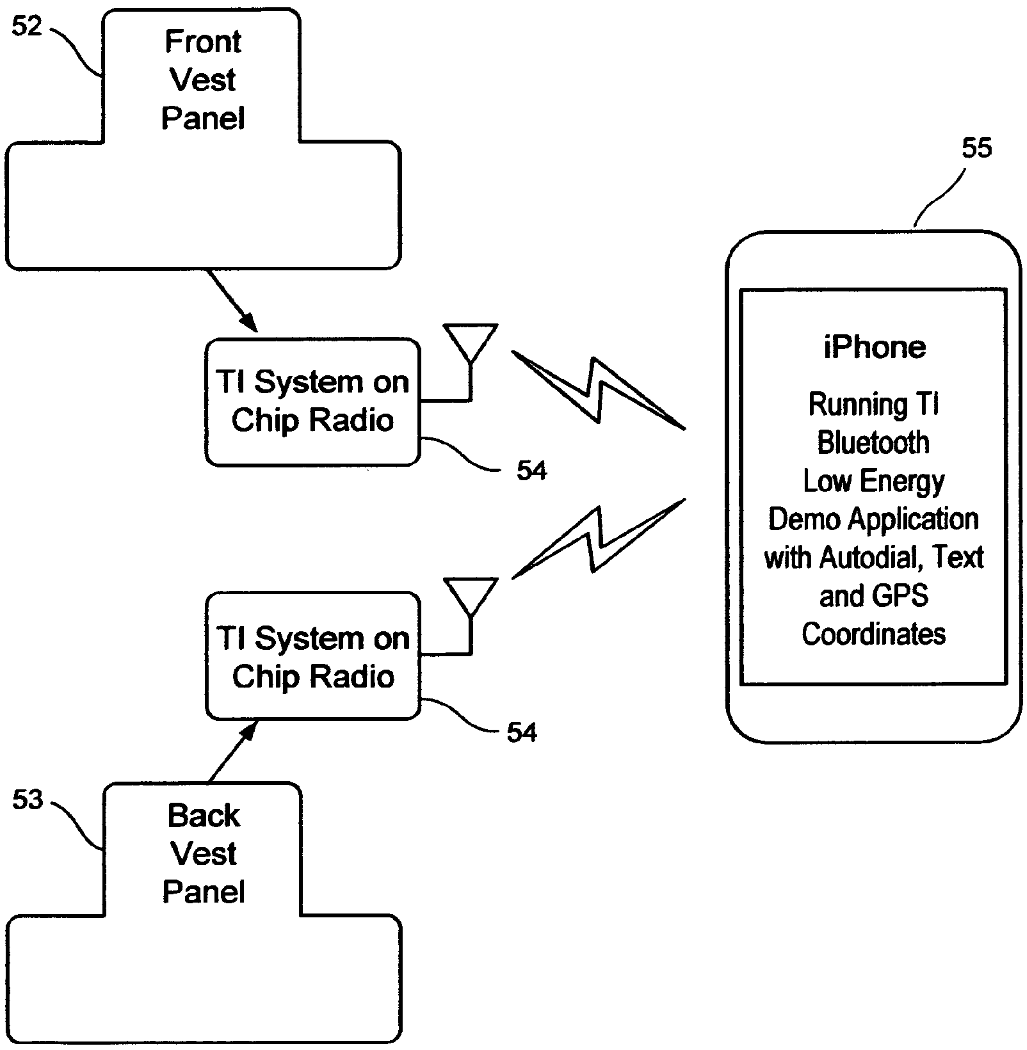
FIG. 7 shows the bullet proof vest embodiment of FIG. 5 of the present disclosure with the second identical panel added and it uses most of existing radio design.

FIG. 7 shows the bullet proof vest embodiment of the present disclosure with the second identical panel 53 added and it uses most of existing radio design 54. This can include but not be limited to late model smart phones 55 with BLE radios (iPhone 4s, etc). An iPhone app can be made to recognize both radios simultaneously.

Figure 8:
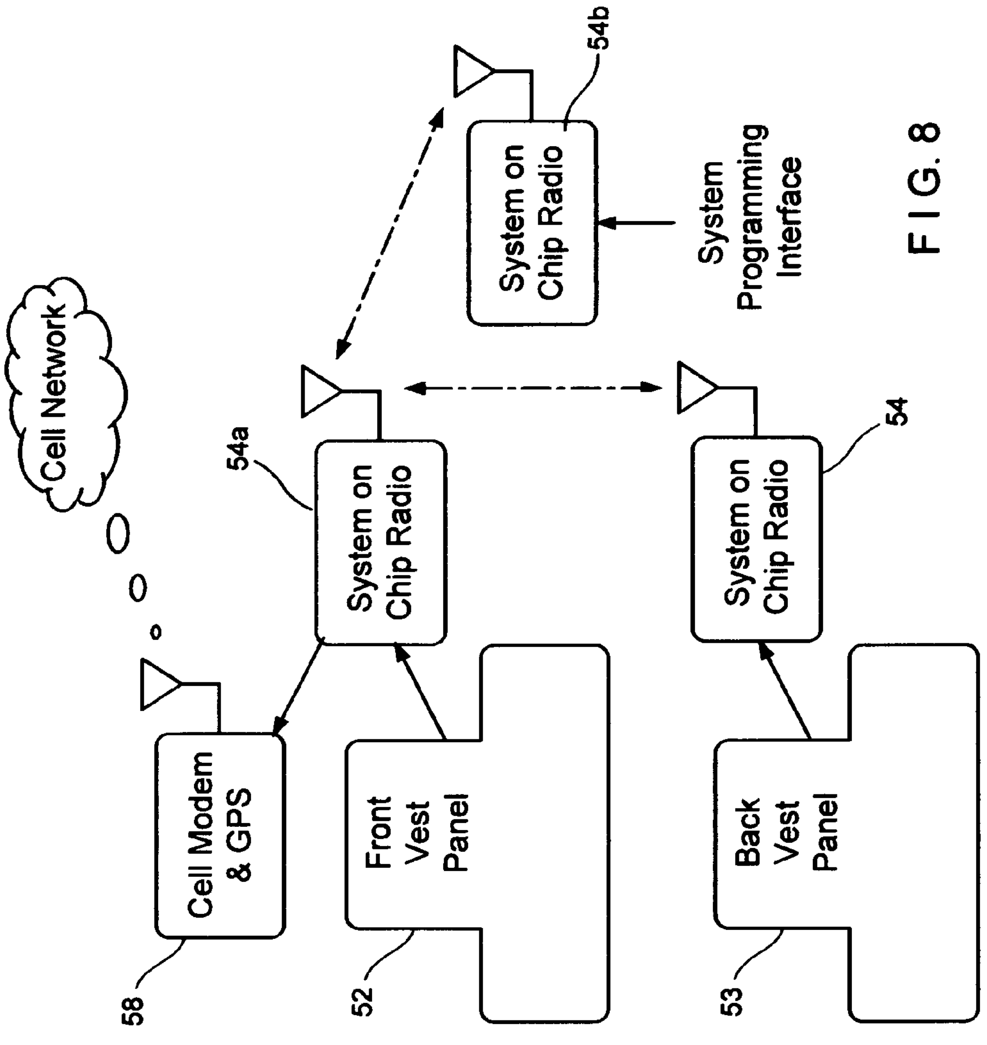
FIG. 8 describes a modified version of the bullet proof vest of the embodiment of FIG. 6 of the present disclosure in which there are changes to the radio supplier and overall system architecture to incorporate a 2G/3G embedded cell modem.

FIG. 8 describes a modified version of the bullet proof vest shown in FIG. 6 in which there are changes to the radio supplier and overall system architecture to incorporate a 2G/3G embedded cell modem 58. One panel 53 (back panel) houses only a BLE radio 54 which senses trace integrity and communicates with other panel's BLE radio 54*a*. Second panel 52 (front panel) incorporates cell modem 58, which when activated, supplies the GPS coordinates, various bits of information associated with officer John E. Law, and makes the call. A follow-on version could be configured to go open mic (microphone) and transmit audio information once the system is activated.

The back panel 53 electronics monitors the integrity of the zone traces (currently upper and lower zones, though the system is not limited to just two zones). When either or both are broken the radio 54 promptly transmits the information using a low power proprietary protocol to the front panel 52 radio 54*a*. The current system utilizes a 2.4 GHz radio frequency link. 54*b*. The radio 54 also periodically transmits a status message to the front panel radio 54*a* verifying integrity of the zones, radio link signal strength, and battery voltage.

As with the back panel 53, the electronics monitors the integrity of the zone traces (currently upper and lower zones, and as with the back, the system is not limited to just two zones). When either or both are broken, or the back panel 53 radio 54 transmits a message indicating one of its zones are broken, the system will promptly transmit the emergency information using the built-in cell phone modem 58 (the current prototype uses a CDMA network for broadest coverage in rural areas). To do this, the front panel electronics will:

apply power to the cell phone modem 58 and GPS 58
verify a valid power-up and cell phone network connection
command the GPS system to acquire the current position
send a text message with zone status information to the programmed phone number(s)
when the GPS coordinates have been calculated (there is a GPS cold start delay), continue to generate additional periodic text messages with both the zone status and the GPS coordinates Should there be an error in any of the system message processing steps; the system will fall back to making a simple 911 call to the emergency dispatcher.

The front panel 52 electronics function as the system gateway to store the user ID and emergency contact numbers, as well as adjust or control any other features that may be incorporated into the system. This information is accessed and programmed with a user interface that links to the front panel 52 electronics over a third 2.4 GHz radio system 54*b* that transfers the information using either Bluetooth or the proprietary protocol. The front panel 52 radio 54*a* uses multi-protocol communication links, whereas the back panel radio 54 only uses a single protocol communication link.

In FIG. 8 the radio 54*a* on the front panel 52 is the main control point of the system. It and the cell modem/GPS 58 share a common circuit located on the front vest panel 52. The radio 54*a* communicates with the back vest panel 53 radio 54 to monitor panel integrity, and is also capable of communicating with a third radio 54*b* when necessary to configure aspects of the system behavior such as user, telephone number, and cell messaging information, or to simply check the system health and status.

Figure 9A:
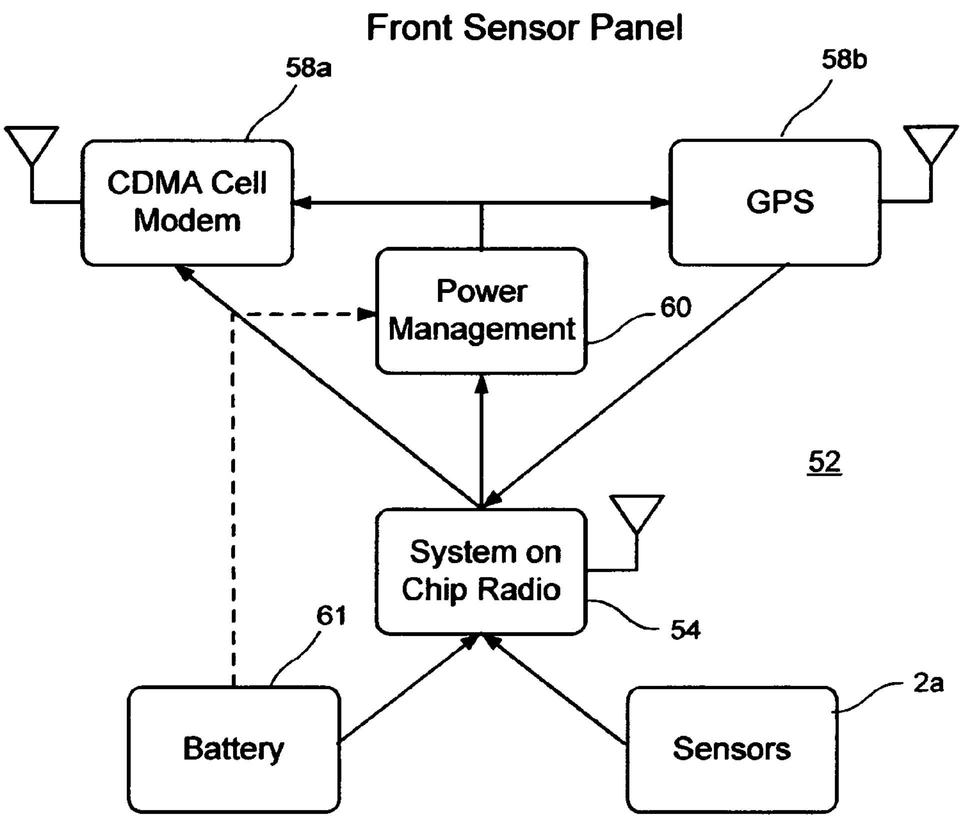
FIGS. 9A and 9B provide a more detailed system description of the individual portions, front panel (FIG. 9A) and back panel (FIG. 9B) of the bullet proof vest embodiment of FIG. 8.
Figure 9B:
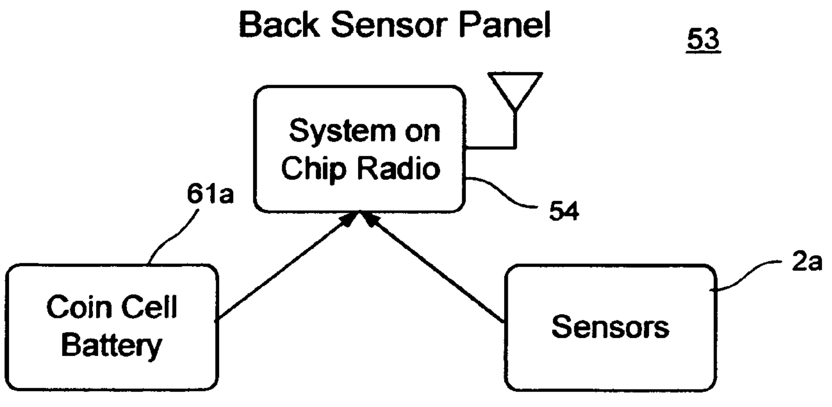

FIGS. 9A and 9B provide a more detailed view of the embodiment, and shows the interrelationship of the system on chip radio 54, sensors 2*a*, batteries 61,61*a*, cell modem 58*a*, power management 60, and GPS sensor 58*b* for both the front and back sensor panels 52,53, respectively. As can be easily seen from the figure, the back panel 53 is both smaller and simpler to implement.

Referring now to FIGS. 9A & 9B, a System on Chip (SoC) is an integrated circuit that incorporates all or most of the parts of an entire electronic system into a single device. The current System on Chip (SoC) device embeds an ARM® Cortex processor with a 2.4 GHz RF transceiver. It also incorporates a number of peripherals for serial communication, timing, encryption, analog conversion, power management, and sensor processing designed specifically for ultra-low power wireless system solutions. In the current embodiment, the front panel SoC uses multiple RF protocols for communication, but the other two radios in the system are single protocol.

Power management component 60 places the system in a low-power state when it is inactive or can turn off power entirely to portions of the system when not needed. The power management feature reduces energy consumption to maximize the battery life of the system, and utilizes a combination of firmware in the SoC 54 as well as sensing and control circuitry to implement these energy reduction techniques. Both low-power states and un-powered subsystems are used in the current embodiment of the design to increase battery life.

The cell modem 58*a* is a device that incorporates the vast majority of a standard cell phone's capabilities, but has been designed for control by a computer or microprocessor using serial or radio communication interfaces, rather than by a person. The current embodiment utilizes a 3G device designed to operate on Code Division Multiple Access (CDMA) cell phone networks.

The Global Positioning System (GPS) block 58*b* is a receiver designed to decode precisely timed navigation signals from a large constellation of satellites from which three dimensional position and velocity information can be determined with relatively high accuracy. In the current embodiment, this receiver and the 3G cell modem 58*a* reside in a common module on the front panel circuit board, and both are controlled and exchange information with the SoC radio using a standard serial communication link. The sensors primarily represent the circuit traces that are being monitored for integrity, but in the current embodiment also include a number of sensors internal to the SoC 54, cell modem, and power management circuitry to provide status and control information to the system.

The batteries are relatively self-explanatory, but the back panel circuitry 53 is extremely small and only requires a small coin cell 61*a* for operation, whereas the front panel batteries 61 must provide sufficient energy to last the multi-year design life of the system, as well as have enough remaining energy at end of life to meet the comparatively large power needs of the cell modem 58*a*. As a result, though both batteries 61, 61*a* are lithium-based chemistries in the current embodiment, the front panel battery 61 is both larger and of a different chemical formulation than the back panel battery 61*a*.

For the below embodiments described in FIGS. 10-12 please note that each of these embodiments for protection of the printed ink/traces or etched copper circuitry can be implemented for the bullet proof vest embodiments of the present invention, the packaging of goods with or without pallets embodiment and for the embodiment for installation of the present invention in floors, walls and/or ceilings as described in the present application.

Figure 10:
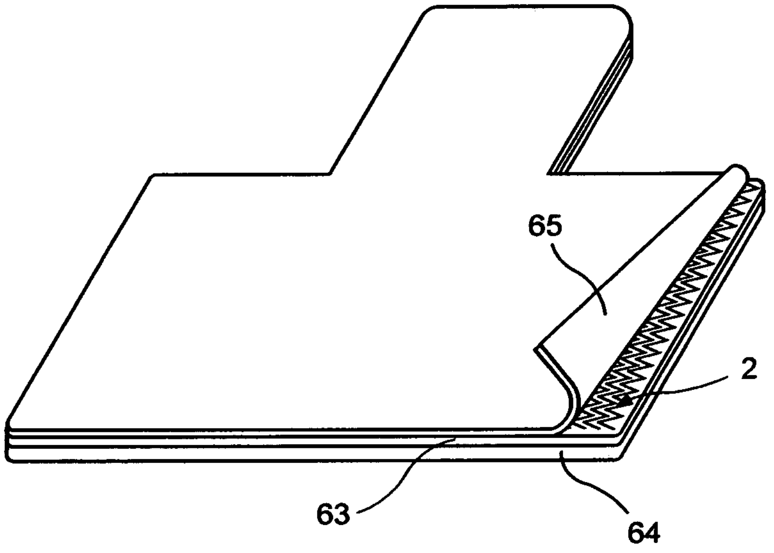
FIG. 10 provides a first embodiment for protecting the printed ink/traces of the present invention.

FIG. 10 illustrates a first embodiment for protecting the printed ink/traces of the present invention from breaking, abrasion or wearing down of the ink and/or traces of the present invention. If there were a break, abrasion or wearing away of the ink/traces for the present invention this could trigger a false alarm that tampering has occurred (or in the case of the bullet proof vest that a bullet shot has hit the vest) when in fact this has not occurred. The protective coating 65 helps to ensure that the ink/traces remain intact unless actual tampering has occurred. In the embodiment of the RTV (Room Temperature Vulcanizing silicone) material 65 (FIG. 10) is applied, preferably uniformly, over the printed ink or traces 2 that can be printed on the Kevlar or Brookwood Ballistic material 63 or any other bulletproof fabric material which in turn can be mounted on the film laminate 2 preferably made of a 10 mil polycarbonate or polyester semi rigid material (for the non bullet proof embodiments the ink/traces are printed directly onto the polycarbonate semi-rigid material without the need for the Kevlar or Brookwood Ballistic material or any other suitable alternative material. Alternatively for the bullet proof embodiment the ink/traces 2 can be printed onto the 10 mil polycarbonate or polyester material 64 which is placed on top of the Kevlar or Brookwood Ballistic material 63. Alternatively for the bullet proof embodiment the ink/traces 2 can be printed directly onto the 10 mil thick polycarbonate or polyester material 64 and a protective layer of 10 mil polycarbonate or polyester material is placed over the base layer and joined to the base layer with adhesive or heat sealing thus protecting the ink/traces 2 from damage.

Figure 11:
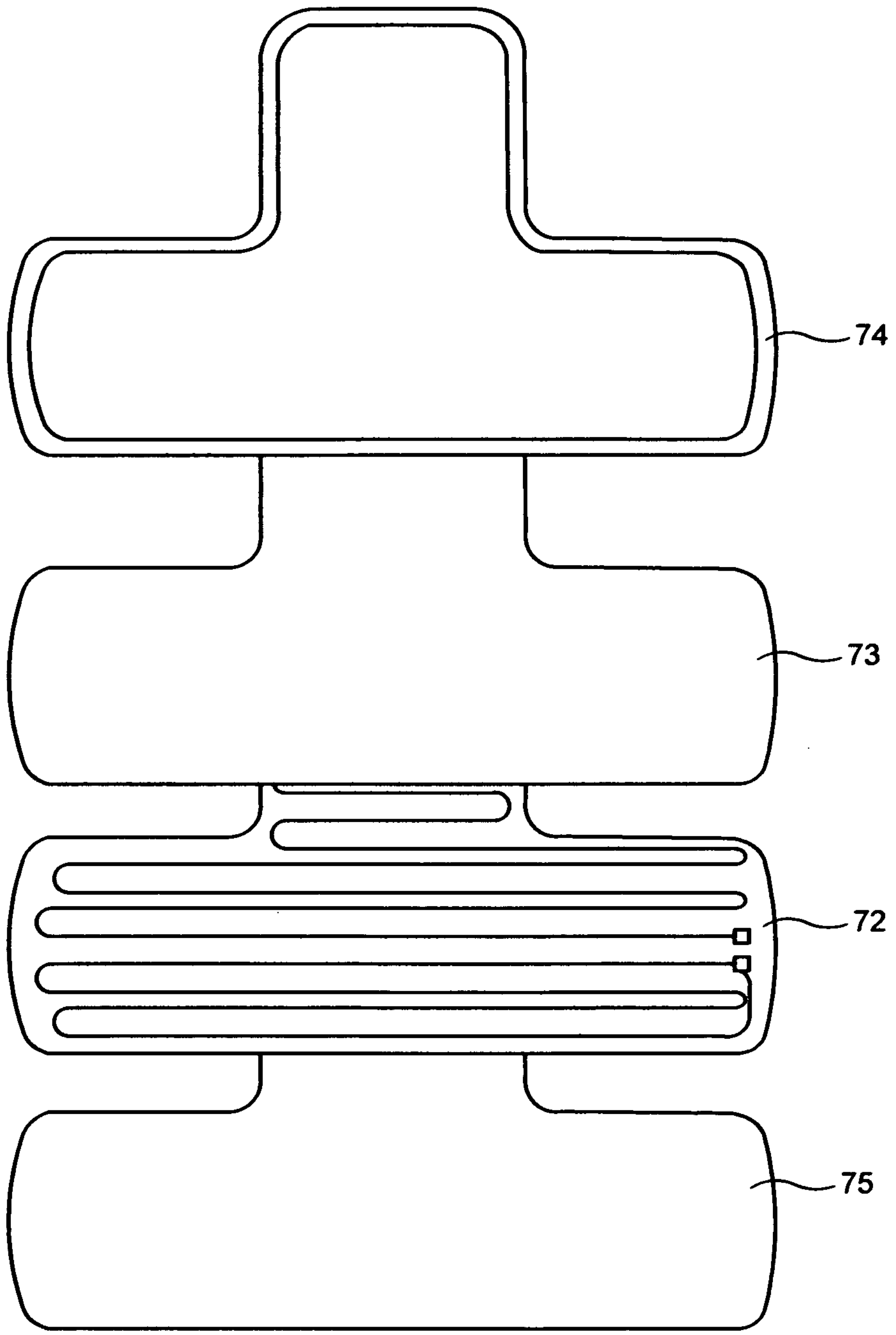
FIG. 11 is an partially exploded view of a second embodiment for protecting the circuitry of the present invention in which copper etchings can be used instead of printed ink/traces.

FIG. 11 shows a partially exploded view of another embodiment for protecting the circuitry of the present invention wherein instead of printed ink/traces, an etched copper circuit 72 is through and underneath the film laminate 2. Here again this protective feature can be utilized with the bullet proof panels, the ceiling/wall/floor, and the packaging with or without a pallet embodiments described in the present application. The edges of the panel have Kapton material housing 73 covering the copper etched circuitry 72 surrounding the perimeter of the panel with additional Kapton material tape 74 covering the border edges of the Kapton material housing to better ensure that that there is no break, abrasion or wearing down of the etched copper circuit to trigger a false alarm that would incorrectly indicate tampering (or a bullet strike in the case of the bullet proof vest embodiments) of the present invention. A Kapton base 75 is provided underneath the etched copper circuitry 72.

Figure 12:
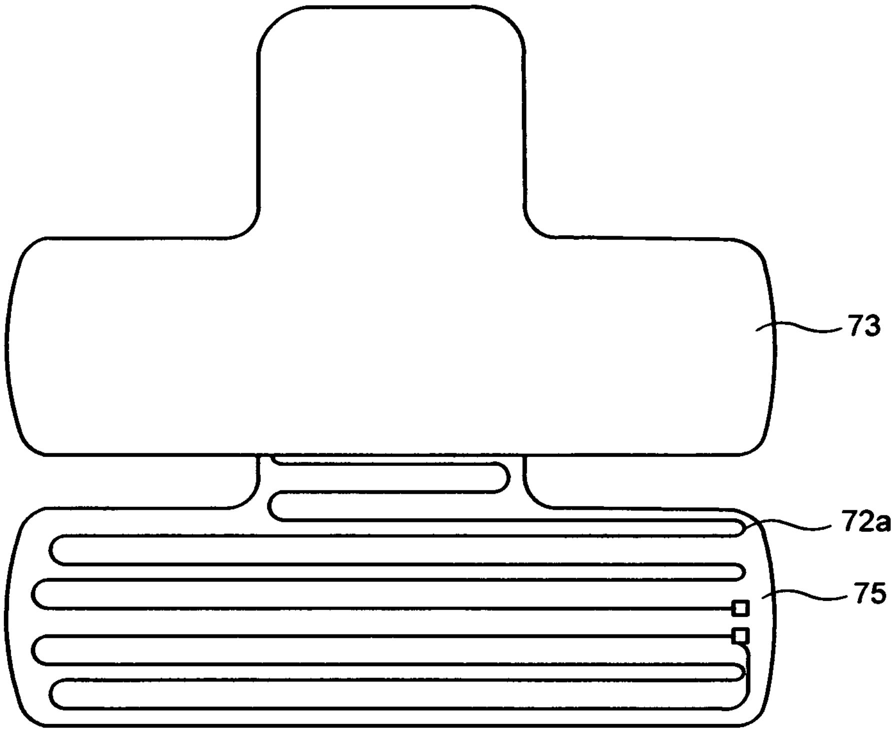
FIG. 12 is an exploded view of another embodiment of the present invention similar to FIG. 11 in which printed ink is provided instead of copper etchings.

FIG. 12 shows a partially exploded view of another embodiment of the present invention in a partially exploded view in which instead of etching copper circuitry, ink or traces 72*a* are printed onto a polycarbonate or polyester base 75 or other suitable commercially available material and on top of this is placed a polycarbonate or polyester cover 73 or other suitable commercially available material. The cover 73 and polycarbonate or polyester base 75 or other suitable commercially available material are both preferably about 10 mil thick.

Another embodiment is in the event an explosion or fire vision is often reduced to touch for both the evacuees and the rescuers. Exit signs during these emergencies just indicate a safe exit during the best circumstances (No fire).

In the event you are in a multi floor building a fire or an explosion can make an exit unsafe and the closest exit may not be the best exit, but with no indication as it stands right now the wrong turn can be fatal.

The solution is to use the tamper indication device 1 as a sensor covering the floors, ceilings and the walls with its low power transceiver providing not only a security function, but also a wire frame of the interior of the building (not shown). With some logic you could turn the exit signs into smart exits indicating the best route to go and provide fire fighter-rescuers for the first time revolutionary near real time status of existing or remaining floors, walls and ceilings. The device can be incorporated into each corner of four corners of a building floor as wells as the ceiling and floor to detect breaches and alert someone as to where the breach is located specifically in the building.

While presently preferred embodiments have been described for purposes of the disclosure, numerous changes in the arrangement of method steps and apparatus parts can be made by those skilled in the art. Such changes are encompassed within the spirit of the invention as defined by the appended claims.

The invention claimed is:

1. A device for monitoring and indicating when a flexible film has been broken or penetrated by an unauthorized individual at a time of the tampering, comprising:

a tamper indication device having a tamper indicating flexible film laminate attached thereto and connected within a circuit that includes an electrically conductive sensor circuit that generates a signal in response to a penetration of said film and therefore penetration of said circuit, said tamper indication device being imprinted with printable conductive ink onto at least portions of a bullet proof vest to provide separate sensor zones on said bullet proof vest to determine a bullet penetration and a location for said bullet penetration based on which of said separate zones is struck and a transponder for receiving said signal which generates an output signal to a display or data collection device, or radio and transceiver to provide a continuous automated passive monitoring of a penetration in the flexible film laminate to provide information as to a penetration in said film laminate and where said penetration has occurred in which of said sensor zones.

2. The device according to claim 1 wherein said bullet proof vest has two separate panels and one of said panels with electrically conductive sensor circuits printed on each panel.

3. The device according to claim 1 wherein each said sensor circuit has circuitry for detecting a bullet penetration and determining the location of the bullet penetration based on a sensor zone of said sensor where the penetration occurred.

4. The device according to claim 1 wherein one of said two panels houses an RF communication device that senses trace integrity and a penetration in said flexible film laminate and said other panel, which also senses trace integrity and a break or penetration in said flexible film laminate, includes a cell phone module or RF communications module with a GPS sensor and said radio communication device in said first panel automatically communicates and activates the cell phone module or RF communications module of said second panel when a penetration of the film is sensed so that when activated by the radio communications device said cell phone module or RF communications module sends GPS coordinates of the bullet strike and wearer identification information to a remote third party.

5. The device according to claim 4 wherein said radio communications device is either a Bluetooth Low energy radio or a Zigbee or RFID communication device.

6. The device according to claim 4 wherein said device includes a microphone to transmit audio information.

7. The device according to claim 1 wherein said transponder is a microcontroller.

8. The device according to claim 1 wherein said transponder is an RFID tag.

9. The device according to claim 3 wherein said RFID tag is an active RFID tag.

10. The device according to claim 3 wherein said RFID tag is a passive RFID tag.

11. The device according to claim 4 wherein said remote third party is either a dispatcher or 911.

12. The device according to claim 1 wherein said transponder for receiving said signal generates an output signal to a smart phone.

* * * * *